United States Patent [19]

Yoneoka et al.

[11] 4,149,009

[45] Apr. 10, 1979

[54] PROCESS FOR PRODUCING METHYL FORMATE

[75] Inventors: Mikio Yoneoka; Minoru Osugi, both of Niigata, Japan

[73] Assignee: Mitsubishi Gas Chemical Co., Inc., Tokyo, Japan

[21] Appl. No.: 853,234

[22] Filed: Nov. 21, 1977

[30] Foreign Application Priority Data

Dec. 2, 1976 [JP] Japan .................................. 51-144899

[51] Int. Cl.² .............................................. C07C 67/40
[52] U.S. Cl. .................................... 560/239; 252/461; 252/463
[58] Field of Search ................ 560/239; 252/461, 463; 260/531 R

[56] References Cited

U.S. PATENT DOCUMENTS

| | | | |
|---|---|---|---|
| 2,522,676 | 9/1950 | Horton | 560/239 |
| 3,188,330 | 6/1965 | Hecker et al. | 560/239 |

Primary Examiner—Vivian Garner
Attorney, Agent, or Firm—Flynn & Frishauf

[57] ABSTRACT

A process for producing methyl formate which comprises dehydrogenating methanol in vapor phase in the presence as a catalyst of copper, zirconium and zinc and optionally aluminum is disclosed.

13 Claims, No Drawings

PROCESS FOR PRODUCING METHYL FORMATE

BACKGROUND OF THE INVENTION

1. Object of the Invention

This invention relates to a process for producing methyl formate which comprises dehydrogenating methanol in vapor phase.

2. Description of the Prior Art

A process for producing methyl formate which comprises dehydrogenating methanol in the presence of certain catalysts is known. For example, a copper catalyst is disclosed in French Pat. No. 673,337, a catalyst obtained by reducing oxides of copper, nickel, chrome and iron (U.S. Pat. No. 1,400,195), and a catalyst obtained by treating copper-aluminum alloy with an aqueous alkaline solution (U.S. Pat. No. 2,504,497), are known as such catalysts. Also, Horton U.S. Pat. No. 2,522,676 discloses a process for producing esters by reacting primary alcohols with sulphur in the absence of any catalyst. In the explanation on the prior art of Horton, Horton states that a mixture of copper and rare metals such as cerium, zirconium or uranium is known as a catalyst for dehydrogenating primary alcohols to form esters. However, these patents do not disclose the yield of methyl formate obtained. We have found that when methanol is dehydrogenated in the presence of copper, methyl formate can not be obtained with excellent selectivity.

We have carried out research for obtaining methyl formate from methanol with high selectivity. As a result, we have found that when methanol is dehydrogenated in vapor phase in the presence of a catalyst comprising copper and at least one element selected from the group consisting of the elements of Group IIIA of the periodic table, the elements of Group IVA of the periodic table, the rare earth elements and the actinide elements as an effective component, methyl formate can be obtained in a high selectivity (refer to U.S. Ser. No. 786,408, filed Apr. 11, 1977, assigned to the assignee of this application). It was found that of these catalysts, a catalyst comprising copper and zirconium gives an excellent selectivity to methyl formate as well as an increased yield of methyl formate. But the activity of the catalyst tended to decrease in a short period.

SUMMARY OF THE INVENTION

We have carried out research for preventing degradation of the activity of the catalyst. As a result, we found a catalyst having a long life. Therefore, this invention relates to a process for producing methyl formate which comprises dehydrogenating methanol in vapor phase in the presence of a catalyst comprising copper, zirconium and zinc or a catalyst comprising copper, zirconium, zinc and aluminum.

DETAILED DESCRIPTION OF THE INVENTION

In the catalyst components employed in the present invention, the atomic ratio of copper to zirconium is 1:0.01 to 2, preferably 1:0.05 to 1; the atomic ratio of copper to zinc is 1:0.01 to 2, preferably 1:0.05 to 1; and the atomic ratio of copper to aluminum is 1:0.01 to 0.5, preferably 1:0.05 to 0.2. A variety of compounds containing copper, zirconium or zinc may be used as a copper source, a zirconium source or a zinc source, respectively. For example, hydroxides, oxides, carbonates, inorganic acid salts or organic acid salts may be used. In particular, basic copper carbonate and basic zinc carbonate are preferred as a copper source and a zinc source, respectively. Zirconium carbonate and zirconium silicate are preferred as a zirconium compound. Zinc zirconate is preferred as a compound containing zirconium and zinc. Aluminasol is preferred as an aluminum source. Blending operations of these compounds may be carried out by adding water to a mixture of these compounds to form a paste, followed by kneading the paste. The operation may be carried out by coprecipitation. Profitably, the catalyst may be produced by a process which comprises drying a mixture of these compounds and baking them at a temperature of about 400° C. in air or nitrogen and then reducing them at about 200° C. in a stream of $H_2$ or CO, thereby activating them.

The dehydrogenation of methanol is carried out by contacting the catalyst with methanol in vapor phase to produce methyl formate. The reaction conditions depend on the catalysts employed. The reaction temperature may be in the range from 100° C. to 400° C., preferably from 150° C. to 350° C.; and space velocity may be in the range of from 100 $hr^{-1}$ to 50,000 $hr^{-1}$, preferably from 500 $hr^{-1}$ to 30,000 $hr^{-1}$; and the reaction may be carried out at atmospheric pressure, a superpressure or a reduced pressure. About 0.01 mol to about 2 mol of a dilution gas, such as hydrogen, carbon monoxide or nitrogen which is non-active to the reactants may be present in the reaction system per 1 mol of methanol. When methyl formate is produced from methanol, selectivity to methyl formate is relative to conversion of methanol. It is preferred to maintain the conversion of methanol at less than 60% in order to keep the selectivity to methyl formate high.

When methyl formate is produced from methanol according to the present invention, selectivity to methyl formate and yield of methyl formate are not only high, but also the catalyst can be used in stable condition for a long period.

The present invention is further illustrated by the following Examples. However, this invention should not be limited by these examples, and the changes and modification within the spirit and scope of this invention can be effected.

Parts and percent are by weight in the following Examples, unless otherwise specified.

EXAMPLE 1

Copper-zirconium-zinc catalyst was prepared by the following process. $ZnZrO_3$ (the atomic ratio of zinc to zirconium is 1:1) was used as a zinc source and a zirconium source.

When a catalyst in which the atomic ratio of zinc to zirconium was more than 1 was used, zinc zirconate and a copper-zinc coprecipitate were used.

When a catalyst in which the atomic ratio of zinc to zirconium was less than 1 was used, basic copper carbonate, zinc zirconate and zirconium carbonate were used.

Basic copper carbonate was prepared in the following way. Each of 1 mol of reagent grade (GR) copper nitrate and 1.17 mol of reagent grade (GR) anhydrous sodium carbonate was dissolved in 1 l of deionized water separately. The solutions were heated to 70° C. and were mixed with each other with strong stirring. The resulting mixture was stirred while maintaining it at 70° C. for one and half hours. The resulting mixture was allowed to stand for one hour with stirring. The precipitate was suction-filtrated from the mixture. The resulting cake was sufficiently washed with deionized water and was dried at 70° C. overnight.

Copper-zinc coprecipitate was prepared in the following way. An aqueous solution of copper nitrate and zinc nitrate having a determined proportion was mixed with an aqueous solution of sodium carbonate at 70° C. to obtain a copper-zinc coprecipitate.

As occasion demanded, each of (a) a mixture of zinc zirconate and copper-zinc coprecipitate and (b) a mixture of basic copper carbonate and zinc zirconate and (c) a mixture of basic copper carbonate, zinc zirconate and zirconium carbonate was prepared. Water was added to each mixture to form a paste. The pastes were blended and kneaded by a kneader for 30 minutes, and were allowed to stand at 70° C. overnight. The resulting dried mixtures were crushed to form particles of 2 to 5 mm size. The particles were baked at 390° C. for one and half hours in air. 3 Percent of graphite was added to each mixture on the basis of the weight of each baked mixture. The mixtures were shaped to tablets 6 mm in diameter and 5 mm high which were then crushed to one-eighth size. The resulting particles containing a copper compound, a zirconium compound and a zinc compound were charged into a pyrex glass pipe having a 20 mm inner diameter, and were maintained at 200° C. for 6 hours in a stream of hydrogen to reduce these compounds, thereby obtaining the catalysts having the proportions as given in Table 1.

A reactor having a 20 mm inner diameter was charged with 10 ml of each of the activated catalysts, and methanol vapor was charged at a space velocity of 3700 hr$^{-1}$ from the edge of the reactor. The reaction was continuously carried out at an atmospheric pressure for 150 hours. The results are shown in Table. 1.

Table 1

| Proportion of catalyst components Cu:Zr:Zn (atomic ratio) | Reaction temperature °C. | | Number of hours from the time when the reaction started | | | |
|---|---|---|---|---|---|---|
| | | | 1 | 50 | 100 | 150 |
| 1:0.3:0.3 | 285 | Conversion of methanol % | 58.5 | 51.5 | 48.0 | 43.7 |
| | | Selectivity to methyl formate % | 83.6 | 90.7 | 91.5 | 92.3 |
| | | Yield of methyl formate % | 48.9 | 46.5 | 43.9 | 40.3 |
| 1:0.3:1 | 305 | Conversion % | 52.8 | 49.9 | 48.7 | 46.8 |
| | | Selectivity % | 86.5 | 88.7 | 90.0 | 90.2 |
| | | Yield % | 45.7 | 44.3 | 43.8 | 42.2 |
| 1:0.3:0.05 | 280 | Conversion % | 57.2 | 49.6 | 46.0 | 42.0 |
| | | Selectivity % | 85.7 | 91.3 | 92.6 | 93.7 |
| | | Yield % | 49.0 | 45.3 | 42.6 | 39.4 |
| 1:1:0.3 | 320 | Conversion % | 50.4 | 45.3 | 42.7 | 38.1 |
| | | Selectivity % | 84.6 | 88.9 | 90.3 | 91.5 |
| | | Yield % | 42.6 | 40.3 | 38.6 | 34.9 |
| 1:0.05:0.3 | 230 | Conversion % | 36.6 | 31.9 | 29.2 | 27.5 |
| | | Selectivity % | 81.5 | 85.3 | 87.6 | 90.1 |
| | | Yield % | 29.8 | 27.2 | 25.6 | 24.8 |

EXAMPLE 2

Copper-zirconium-zinc-aluminum catalysts having the proportions as given in the following were prepared by the following process. An aqueous solution of copper nitrate and zinc nitrate having a determined proportion was mixed with an aqueous solution of sodium carbonate at 70° C. to obtain a copper-zinc coprecipitate. The coprecipitate was filtered and washed with water. To the coprecipitate was added zirconium carbonate and aluminasol so as to prepare catalysts having the following proportions. The resulting pastes were blended and kneaded by a kneader. The pastes were dried at 70° C. overnight and baked at 390° C. in air and shaped to tablets which were crushed to one-eighth size thereof and reduced at 200° C. in a stream of hydrogen. Catalysts A were prepared according to the above process.

Basic copper carbonate, zinc zirconate and aluminasol were mixed, kneaded and treated as the same way as above method so as to prepare the catalysts having the proportion of catalyst B.

A reactor having a 20 mm inner diameter was filled with 10 ml of each of the activated catalysts, methanol vapor was charged at space velocity of 3850 hr$^{-1}$ from the edge of the reactor. The reaction was continuously carried out at an atmospheric pressure for 150 hours. The results are shown in Table 2.

Table 2

| Proportion of catalyst components Cu:Zr:Zn:Al (atomic ratio) | Reaction temperature ° C. | | Number of hours from the time when the reaction started | | | |
|---|---|---|---|---|---|---|
| | | | 1 | 50 | 100 | 150 |
| Catalyst A | | | | | | |
| 1:0.3:0.3:0.1 | 300 | Conversion of methanol % | 58.3 | 54.3 | 53.1 | 52.0 |
| | | Selectivity to methyl formate % | 84.6 | 90.0 | 91.7 | 91.9 |
| | | Yield of methyl formate % | 49.3 | 48.9 | 48.7 | 47.8 |
| 1:0.3:0.1:0.1 | 285 | Conversion % | 61.5 | 54.5 | 51.2 | 49.5 |
| | | Selectivity % | 79.9 | 88.5 | 92.3 | 92.7 |
| | | Yield % | 49.1 | 48.2 | 47.3 | 45.9 |
| 1:0.3:1:0.1 | 310 | Conversion % | 63.2 | 54.9 | 53.5 | 52.0 |
| | | Selectivity % | 76.8 | 88.5 | 90.1 | 91.0 |
| | | Yield % | 48.5 | 48.6 | 48.2 | 47.3 |
| 1:1:0.3:0.1 | 330 | Conversion % | 49.9 | 46.6 | 45.5 | 44.2 |
| | | Selectivity % | 87.6 | 90.3 | 90.7 | 90.6 |
| | | Yield % | 43.7 | 42.1 | 41.3 | 40.0 |
| 1:0.05:0.3:0.1 | 235 | Conversion % | 34.8 | 32.7 | 31.4 | 29.0 |
| | | Selectivity % | 82.3 | 86.0 | 87.9 | 90.7 |
| | | Yield % | 28.6 | 28.1 | 27.6 | 26.3 |
| 1:0.3:0.3:0.05 | 295 | Conversion % | 57.2 | 53.0 | 50.4 | 48.5 |
| | | Selectivity % | 85.5 | 89.8 | 91.1 | 91.3 |
| | | Yield % | 48.9 | 47.6 | 45.9 | 44.3 |
| 1:0.3:0.3:0.2 | 285 | Conversion % | 60.7 | 55.7 | 52.1 | 48.8 |
| | | Selectivity % | 76.6 | 81.3 | 85.6 | 87.9 |
| | | Yield % | 46.5 | 45.3 | 44.6 | 42.9 |
| Catalyst B | | Conversion % | 62.0 | 52.6 | 52.1 | 50.8 |

Table 2-continued

| Proportion of catalyst components Cu:Zr:Zn:Al (atomic ratio) | Reaction temperature °C. | | Number of hours from the time when the reaction started | | | |
|---|---|---|---|---|---|---|
| | | | 1 | 50 | 100 | 150 |
| 1:0.3:0.3:0.1 | 285 | Selectivity % | 79.7 | 90.5 | 91.6 | 92.3 |
| | | Yield % | 49.4 | 47.6 | 47.7 | 46.9 |

COMPARATIVE EXAMPLE 1

Basic copper carbonate powder prepared by the same method as in Example 1, and zirconium carbonate were mixed and kneaded to obtain a catalyst of which the atomic ratio of Cu:Zr is 1:0.3.

This mixture was reduced in the same way as in Example 1 to obtain a catalyst comprising Cu and Zr. The catalyst is the one described in said Horton patent. The dehydrogenating reaction of Example 1 was repeated except that the space velocity is 4000 hr$^{-1}$ and the reaction temperature is 270° C. The results are as in Table 3.

Table 3

| | Number of hours from the time when the reaction started | | | |
|---|---|---|---|---|
| | 1 | 50 | 100 | 150 |
| Conversion of methanol % | 56.8 | 4.9 | 1.6 | 0.6 |
| Selectivity to methyl formate % | 84.0 | 94.0 | 93.7 | 93.1 |
| Yield of methyl formate % | 47.7 | 4.6 | 1.5 | 0.6 |

It is apparent from Comparative Example 1 and Table 3 that a catalyst comprising copper and zirconium is degraded in 50 hours, whereas the present catalyst is not degraded to a considerable extent even after 150 hours (Table 2).

What is claimed is:

1. A process for producing methyl formate, characterized by dehydrogenating methanol in vapor phase in the presence of a catalyst consisting essentially of copper, zirconium and zinc.

2. The process as claimed in claim 1 in which the atomic ratio of copper:zirconium:zinc is 1:0.01 to 2:0.01 to 2.

3. The process as claimed in claim 1 in which the copper component in the catalyst is one obtained by baking basic copper carbonate, and the zinc component therein is one obtained by baking basic zinc carbonate.

4. The process as defined in claim 1 wherein the dehydrogenation is carried out in the presence of a dilution gas.

5. The process as defined in claim 1 wherein the dehydrogenation is carried out at a space velocity in the range of from 100 hr$^{-1}$ to 50,000 hr$^{-1}$.

6. The process as defined in claim 1 wherein the dehydrogenation is carried out at a temperature in the range of from 100° C. to 400° C.

7. A process for producing methyl formate, characterized by dehydrogenating methanol in vapor phase in the presence of a catalyst consisting essentially of copper, zirconium, zinc and aluminum.

8. The process as claimed in claim 7 in which the atomic ratio of copper:zirconium:zinc:aluminum is 1:0.01 2:0.01 to 2:0.01 to 0.5.

9. The process as claimed in claim 7 in which the copper component in the catalyst is one obtained by baking basic copper carbonate, and the zinc component therein is one obtained by baking basic zinc carbonate.

10. The process as claimed in claim 7 in which aluminasol is used as an aluminum source.

11. The process as defined in claim 7 wherein the dehydrogenation is carried out in the presence of a dilution gas.

12. The process as defined in claim 7 wherein the dehydrogenation is carried out at a space velocity in the range of from 100 hr$^{-1}$ to 50,000 hr$^{-1}$.

13. The process as defined in claim 7 wherein the dehydrogenation is carried out at a temperature in the range of from 100° C. to 400° C.

* * * * *